United States Patent
Hansen et al.

(10) Patent No.: US 8,454,997 B2
(45) Date of Patent: Jun. 4, 2013

(54) SOLID DOSE MICRO IMPLANT

(75) Inventors: Henrik Egesborg Hansen, Hellerup (DK); Thomas Buch-Rasmussen, Gentofte (DK); Mads Christian Sabra, Kobenhavn (DK)

(73) Assignee: Novo Nordisk A/S, Bagsvaerd (DK)

( * ) Notice: Subject to any disclaimer, the term of this patent is extended or adjusted under 35 U.S.C. 154(b) by 693 days.

(21) Appl. No.: 10/322,143

(22) Filed: Dec. 18, 2002

(65) Prior Publication Data

US 2003/0161881 A1 Aug. 28, 2003

Related U.S. Application Data

(60) Provisional application No. 60/342,065, filed on Dec. 19, 2001.

(30) Foreign Application Priority Data

Dec. 18, 2001 (DK) .................................. 2001 01901

(51) Int. Cl.
*A61K 9/22* (2006.01)

(52) U.S. Cl.
USPC .......................................... 424/468; 424/486

(58) Field of Classification Search
USPC ......................................................... 424/468
See application file for complete search history.

(56) References Cited

U.S. PATENT DOCUMENTS

| | | |
|---|---|---|
| 3,948,263 A | 4/1976 | Drake, Jr. et al. |
| 4,015,033 A | 3/1977 | Nield |
| 4,089,334 A | 5/1978 | Schwebel et al. |
| 4,153,406 A | 5/1979 | Dittman et al. |
| 4,576,604 A | 3/1986 | Guittard et al. |
| 4,671,953 A | 6/1987 | Stanley et al. |
| 4,697,575 A | 10/1987 | Horowitz |
| 4,920,727 A | 5/1990 | Ristimaki et al. |
| 4,962,091 A | 10/1990 | Eppstein et al. |
| 5,153,002 A | 10/1992 | McMullen et al. |
| 5,356,635 A | 10/1994 | Raman et al. |
| 5,372,590 A | 12/1994 | Haber et al. |
| 5,403,595 A | 4/1995 | Kitchell et al. |
| 5,429,822 A | 7/1995 | Gresser et al. |
| 5,434,146 A | 7/1995 | Labrie et al. |
| 5,486,362 A | 1/1996 | Kitchell et al. |
| 5,525,352 A | 6/1996 | Kontos et al. |
| 5,536,503 A | 7/1996 | Kitchell et al. |
| 5,541,172 A | 7/1996 | Labrie et al. |
| 5,542,920 A | 8/1996 | Cherif Cheikh |
| 5,543,156 A | 8/1996 | Roorda et al. |
| 5,567,439 A | 10/1996 | Myers et al. |
| 5,582,591 A | 12/1996 | Cheikh |
| 5,595,760 A | 1/1997 | Cherif-Cheikh |
| 5,616,123 A | 4/1997 | Cheikh |
| 5,629,303 A | 5/1997 | Labrie et al. |
| 5,633,000 A | 5/1997 | Grossman et al. |
| 5,656,298 A | 8/1997 | Kitchell et al. |
| 5,660,846 A | 8/1997 | Cheikh |
| 5,695,463 A | 12/1997 | Cherif-Cheikh |
| 5,716,981 A | 2/1998 | Hunter et al. |
| 5,762,961 A | 6/1998 | Roser et al. |
| 5,766,637 A | 6/1998 | Shine et al. |
| 5,776,107 A | 7/1998 | Cherif-Cheikh |
| 5,783,567 A | 7/1998 | Hedley et al. |
| 5,814,340 A | 9/1998 | Labrie et al. |
| 5,817,343 A | 10/1998 | Burke |
| 5,823,994 A | 10/1998 | Sharkey et al. |
| 5,833,891 A | 11/1998 | Subramaniam et al. |
| 5,837,276 A | 11/1998 | Cheikh |
| 5,851,547 A | 12/1998 | Fujioka et al. |
| 5,858,388 A | 1/1999 | Grossman et al. |
| 5,861,387 A | 1/1999 | Labrie et al. |
| 5,874,029 A | 2/1999 | Subramaniam et al. |
| 5,882,682 A | 3/1999 | Rork et al. |
| 5,886,026 A | 3/1999 | Hunter et al. |
| 5,929,196 A | 7/1999 | Kissel et al. |
| 5,945,128 A | 8/1999 | Deghenghi |
| 5,980,948 A | 11/1999 | Goedemoed et al. |
| 5,994,341 A | 11/1999 | Hunter et al. |
| 6,004,573 A | 12/1999 | Rathi et al. |

(Continued)

FOREIGN PATENT DOCUMENTS

| | | |
|---|---|---|
| CA | 1 196 864 | 11/1985 |
| CA | 1196864 | * 11/1985 |

(Continued)

OTHER PUBLICATIONS

Yamakawa et al. Sustained release of insulin by double-layered implant using poly(D,L-lactic acid). Journal of Pharmaceutical Sciences. vol. 29, No. 6, 1990, pp. 505-509.*

Yamakawa et al (Sustained release of insulin by double-layered implant using poly(D,L-lactic acid). Journal of Pharmaceutical Sciences. vol. 79, No. 6, 1990, pp. 505-509).*

International Search Report issued in connection with counterpart International Application No. PCT/DK02/00865, mailed Apr. 10, 2003.

(Continued)

*Primary Examiner* — Jake M. Vu (74) *Attorney, Agent, or Firm* — Wesley A. Nicolas; Marc A. Began; Reza Green (57) ABSTRACT

A solid pharmaceutical composition for parenteral administration having an inner matrix containing at least one therapeutic agent, and a biodegradable, and water-impermeable coating covering part of the surface of said composition. The inner matrix disintegrates upon contact with animal tissue or tissue fluids. By providing a disintegratable and/or soluble inner matrix comprising the drug with a water-impermeable coating covering part of the surface of said composition, the rate of release of the drug can be controlled. The specific rate of release can be controlled by carefully designing the part of the surface which is not covered.

49 Claims, 3 Drawing Sheets

U.S. PATENT DOCUMENTS

| | | | |
|---|---|---|---|
| 6,077,523 | A | 6/2000 | Deghenghi |
| 6,098,675 | A | 8/2000 | Runft |
| 6,117,949 | A | 9/2000 | Rathi et al. |
| 6,126,956 | A | 10/2000 | Grossman et al. |
| 6,139,574 | A | 10/2000 | Vacanti et al. |
| 6,143,037 | A | 11/2000 | Goldstein et al. |
| 6,149,864 | A | 11/2000 | Dillow et al. |
| 6,159,490 | A | 12/2000 | Deghenghi |
| 6,176,874 | B1 | 1/2001 | Vacanti et al. |
| 6,183,781 | B1 | 2/2001 | Burke |
| 6,193,994 | B1 | 2/2001 | Lee et al. |
| 6,197,575 | B1 | 3/2001 | Griffith et al. |
| 6,201,072 | B1 | 3/2001 | Rathi et al. |
| 6,224,630 | B1 | 5/2001 | Bao et al. |
| 6,224,794 | B1 | 5/2001 | Amsden et al. |
| 6,231,904 | B1 | 5/2001 | Mueller |
| 6,232,340 | B1 | 5/2001 | Zhang et al. |
| 6,241,771 | B1 | 6/2001 | Gresser et al. |
| 6,290,991 | B1 | 9/2001 | Roser et al. |
| 6,485,453 | B1 | 11/2002 | Buch-Rasmussen et al. |
| 2002/0111603 | A1 | 8/2002 | Cheikh |
| 2003/0054044 | A1 | 3/2003 | Potter et al. ............. 424/489 |
| 2003/0161881 | A1 | 8/2003 | Hansen et al. |
| 2003/0234466 | A1 | 12/2003 | Rasmussen et al. |
| 2005/0202072 | A1 | 9/2005 | Buch-Rasmussen et al. |

FOREIGN PATENT DOCUMENTS

| | | |
|---|---|---|
| EP | 0 049 068 B1 | 12/1985 |
| EP | 0 838 209 | 4/2000 |
| EP | 0 838 209 A1 | 4/2000 |
| EP | 1 092 433 A2 | 4/2001 |
| GB | 2 091 554 A | 4/1982 |
| JP | 59-167513 | 9/1984 |
| JP | 11508224 | 2/1992 |
| JP | 05-255071 | 10/1993 |
| JP | 6321803 A | 11/1994 |
| WO | WO 92/02211 * | 2/1992 |
| WO | WO 92/02211 A1 | 2/1992 |
| WO | WO 93/10758 A1 | 6/1993 |
| WO | WO 93/17662 A1 | 9/1993 |
| WO | WO 93/23110 A1 | 11/1993 |
| WO | WO 94/22423 A1 | 10/1994 |
| WO | WO 94/24263 A1 | 10/1994 |
| WO | WO 96/03978 A1 | 2/1996 |
| WO | 96/07397 | 3/1996 |
| WO | 96/07398 | 3/1996 |
| WO | 96/07440 | 3/1996 |
| WO | WO 96/07397 A2 | 3/1996 |
| WO | WO 96/07397 A3 | 3/1996 |
| WO | WO 96/07398 A2 | 3/1996 |
| WO | WO 96/07440 A2 | 3/1996 |
| WO | WO 96/07440 A3 | 3/1996 |
| WO | WO 96/08289 A1 | 3/1996 |
| WO | 98/32427 | 7/1998 |
| WO | WO 99/33853 A2 | 7/1999 |
| WO | 00/32071 | 6/2000 |
| WO | 00/53160 | 9/2000 |
| WO | 00/62759 | 10/2000 |
| WO | WO 00/62759 A1 * | 10/2000 |
| WO | 01/35932 | 5/2001 |
| WO | 01/37804 | 5/2001 |

OTHER PUBLICATIONS

Written Opinion issued in connection with counterpart International Application No. PCT/DK02/00865, mailed Aug. 11, 2003.
International Preliminary Examination Report issued in connection with counterpart International Application No. PCT/DK02/00865, mailed Mar. 13, 2004.
Office Action issued in connection with counterpart European Application No. 02787456.9, mailed Nov. 22, 2006.
Office Action dated Jan. 29, 2008 in U.S. Appl. No. 11/052,645, filed Feb. 7, 2005 by Buch-Rasmussen et al.
Response to Feb. 25, 2008 Office Action in U.S. Appl. No. 10/341,142, submitted May 29, 2008.
Response to Office Action dated Jan. 29, 2008 in U.S. Appl. No. 11/052,645, submitted Jun. 26, 2008.
Response submitted Feb. 5, 2009 in U.S. Appl. No. 10/341,142, filed Jan. 13, 2003 by Buch-Rasmussen et al.
Office Action dated Oct. 17, 2008 in U.S. Appl. No. 11/052,645, filed Feb. 7, 2005 by Buch-Rasmussen et al.
Response submitted Feb. 17, 2009 in U.S. Appl. No. 11/052,645, filed Feb. 7, 2005 by Buch-Rasmussen et al.
Machine English language translation of JP 11508224.
English Abstract of JP 59-167513.
Office Action dated Feb. 25, 2008 in U.S. Appl. No. 10/341,142 by Buch-Rasmussen et al., filed Jan. 13, 2003.
Office Action dated May 8, 2008 in U.S. Appl. No. 10/322,143 by Hansen et al., filed Dec. 18, 2002.
Office Action dated Sep. 5, 2008 in U.S. Appl. No. 10/341,142 by Buch-Rasmussen et al., filed Jan. 13, 2003.
Office Action dated Sep. 29, 2008 in U.S. Appl. No. 10/322,143 by Hansen et al., filed Dec. 18, 2002.
Non-Final Office Action dated Jul. 3, 2006 in U.S. Appl. No. 10/341,142, filed Jan. 13, 2003 by Rasmussen.
Final Office Action dated Mar. 13, 2007 in U.S. Appl. No. 10/341,142, filed Jan. 13, 2003 by Rasmussen.
Non-Final Office Action dated Sep. 18, 2007 in U.S. Appl. No. 10/341,142, filed Jan. 13, 2003 by Rasmussen.
Non-Final Office Action dated Feb. 25, 2008 in U.S. Appl. No. 10/341,142, filed Jan. 13, 2003 by Rasmussen.
Non-Final Office Action dated Sep. 5, 2008 in U.S. Appl. No. 10/341,142, filed Jan. 13, 2003 by Rasmussen.
Final Office Action dated Apr. 20, 2009 in U.S. Appl. No. 10/341,142, filed Jan. 13, 2003 by Rasmussen.
Non-Final Office Action dated Nov. 9, 2009 in U.S. Appl. No. 10/341,142, filed Jan. 13, 2003 by Rasmussen.
Non-Final Office Action dated Oct. 6, 2005 in U.S. Appl. No. 10/322,143, filed Dec. 18, 2002 by Hansen.
Final Office Action dated Jul. 5, 2006 in U.S. Appl. No. 10/322,143, filed Dec. 18, 2002 by Hansen.
Advisory Action dated Jan. 22, 2007 in U.S. Appl. No. 10/322,143, filed Dec. 18, 2002 by Hansen.
Non-Final Office Action dated Oct. 31, 2007 in U.S. Appl. No. 10/322,143, filed Dec. 18, 2002 by Hansen.
Final Office Action dated May 8, 2008 in U.S. Appl. No. 10/322,143, filed Dec. 18, 2002 by Hansen.
Non-Final Office Action dated Sep. 29, 2008 in U.S. Appl. No. 10/322,143, filed Dec. 18, 2002 by Hansen.
Final Office Action dated Jul. 15, 2009 in U.S. Appl. No. 10/322,143, filed Dec. 18, 2002 by Hansen.
Non-Final Office Action dated Jan. 19, 2010 in U.S. Appl. No. 10/322,143, filed Dec. 18, 2002 by Hansen.
Non-Final Office Action Mailed Nov. 29, 2010 in U.S. Appl. No. 10/322,143, filed Dec. 18, 2002; First Named Inventor: Henrik Egesborg Hansen.
Written Opinion issued in connection with counterpart PCT Application No. PCT/DK01/00489, mailed Jun. 11, 2002.
International Preliminary Examination Report and accompanied Annex issued in connection with counterpart PCT Application No. PCT/DK01/00489, mailed Sep. 26, 2002.
Office Action issued in connection with counterpart European Application No. 01 960 172.3, mailed Mar. 2, 2006.
Office Action dated Jan. 29, 2008 in U.S. Appl. No. 11/052,645 by Buch-Rasmussen et al., filed Feb. 7, 2005.
Office Action dated Oct. 17, 2008 in U.S. Appl. No. 11/052,645 by Buch-Rasmussen et al., filed Feb. 7, 2005.
Final Office Action dated Jul. 15, 2009 in U.S. Appl. No. 10/322,143 by Hansen et al., filed Dec. 18, 2002.

* cited by examiner

SOLID DOSE MICRO IMPLANT

CROSS-REFERENCE TO RELATED APPLICATIONS

This application claims priority under 35 U.S.C. 119 of Danish application no. PA 2001 01901 filed Dec. 18, 2001 and U.S. application No. 60/342,065 filed Dec. 19, 2001, the contents of which are fully incorporated herein by reference

TECHNICAL AREA

The invention relates to a solid pharmaceutical composition comprising at least one pharmaceutical agent, to the use of the pharmaceutical composition and to methods for producing pharmaceutical compositions according to the invention.

PRIOR ART

By far the most widely used method for parenteral injection of drugs is by injection of an aqueous solution using a hypodermic syringe. The use of aqueous solutions is associated with a number of inherent problems. In order to inject a given volume of drug, a much larger volume of water and different additives also have to be injected. Weight ratios of drug to solvent may be in the range of 1:100 to 1:1,000. For intramuscular injection, the pain associated with injection is primarily caused by the volume injected, not by the penetration of the skin. Any reduction in volume would thus lead to a reduction in pain for the patient.

Furthermore, it has turned out that the bioavailability of drugs injected as part of a solution varies from individual to individual and from time to time, because the ability to take up the drug varies from person to person and because the rate of uptake is highly dependent on the exact location of the injected solution in the tissue. A further source of variation is the volume over which the injected solution spreads when injected. Drugs that are injected as powder or particles suffer from the same drawbacks, since they may also be injected in different locations and be spread over a different volume of tissue every time. The most reproducible results are obtained by injecting one solid composition, which will occupy the same volume in the tissue every time it is injected and which has the same area of contact with the tissue fluids every time.

For some drugs, the solubility in water is very low. This has two consequences. Either the solutions become dilute and thereby the injection volume increases. Or, additives such as surfactants must be added to the solution to increase the concentration of active ingredient. Such additives or surfactants are potentially toxic. The potential for toxicity greatly limits the possibilities for developing formulations, thus potentially limiting the availability of important drugs.

Generally, an aqueous solution of any given drug is chemically less stable than a dry formulation of the same drug. Furthermore, an aqueous solution is prone to microbial contamination and needs to be sterilised by use of heat, radiation, filtration or chemical means. To increase the shelf life of aqueous drug formulations preservatives, stabilisers, antioxidants, biocides etc are often added. These additives may also add to the toxicity of the formulation. Alternatively or additionally, the aqueous solutions may require special storage conditions at low temperature to avoid chemical or microbial break down of the active ingredients and to avoid microbial growth.

U.S. Pat. No. 5,851,547 relates to a solid dose drug formulation with an inner non-disintegrating matrix comprising a therapeutic agent and an outer layer being made from a hydrophobic polymer. The outer layer can be made from biodegradable materials such as PLGA or from non-biodegradable material such as EVA or Silastic Medical Grade ETR Elastomer. It is emphasised that the inner layer must be made from a non-disintegrating material. The preferred material is silicone. By using the solid dose formulation the rate of release of the therapeutic agent is diminished and approximately constant release over prolonged periods (30 to 120 days) is obtained. However due to the slow release of the drug from this formulation, it is not adapted for administration of drugs, which are injected e.g. daily. Furthermore, the materials used for the inner non-disintegrating matrix are non-degradable in human tissue and must be removed surgically from the body.

U.S. Pat. No. 6,126,956 discloses another coated solid dose drug formulation, wherein the inner matrix comprises ethylen vinyl acetat co-polymer, which is non-biodegradable. The solid dose is coated with e.g. polymethylmethacrylat (PMMA) to slow down the rate of release of the drug. Release takes place through a hole in the coat to give an approximately constant rate of release. The disclosed release profiles show that approximately sustained release can take place for periods up to 90 days. The reference discloses no details about the rate of release during the first hours after the solid dose drug formulation has been inserted into the body. The solid dose drug formulation being made from materials that are non-biodegradable has to be removed surgically from the body after the drug has been released.

U.S. Pat. No. 5,153,002 discloses a cylindrical solid dose drug formulation being coated on the curved sides, and one of the ends. In the inner matrix solid particles of a therapeutic agent are embedded, the amount of therapeutic agent being highest in the end furthest away from the open end of the formulation. According to the reference this provides a constant release. It is emphasised that the inner matrix must not dissolve or disintegrate before the therapeutic agent has been released. This means that the body of the inner matrix remains in the tissue for a substantial time after release of the therapeutic agent causing local irritation to the tissue.

PCT/DK00/00184 (Novo Nordisk A/S) discloses a solid pharmaceutical composition for parenteral injection comprising a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix, and the amount of said therapeutic agent consisting at least one dosage. The pharmaceutical composition has the strength to be injected directly without the need for cannulas, trocars or the like. The therapeutic agent may be any pharmaceutical suitable for injection, such as subcutaneous or intramuscular injection. Pharmaceutical compositions according to this disclosure are easy to manufacture store, and administer. However, the binder, being based on carbohydrates dissolves very rapidly after injection releasing a boost of the therapeutic agent shortly after injection.

Generally in the art, methods are known for manufacturing solid dose formulation in the shape of powder, crystals, pellets, rods or tablets. These methods comprise spray drying, extrusion, compression such as described in PCT/DK00/00570 (Novo Nordisk) or moulding such as injection moulding as for example described in PCT/DK00/00184 quoted above.

SUMMARY OF THE INVENTION

According to a first aspect the invention relates to a solid pharmaceutical composition for parenteral administration comprising an inner matrix comprising at least one therapeutic agent, and a biodegradable, and water-impermeable coating covering part of the surface of said composition, wherein said inner matrix disintegrates upon contact with animal tissue or tissue fluids.

By providing a disintegratable and/or soluble inner matrix comprising the drug with a water-impermeable coating covering part of the surface of said composition, the rate of release of the drug can be controlled. The specific rate of release can be controlled by carefully designing the part of the surface which is not covered. All compositions according to the invention have a release profile with a smaller peak and longer duration compared to non-coated compositions. For therapeutic agents, where a certain minimum presence in the body is required the amount of injected therapeutic agent can be diminished and/or the interval between administration be increased. By having a more constant release rate of the therapeutic agent, less unwanted side effects are observed.

A further advantage of the compositions according to the present invention is that the whole composition is broken down completely in the tissue within relatively short time in comparison to the time required for release of the therapeutic agent. Accordingly, no surgery is required to remove the composition after release of the therapeutic agent and the amount of local irritation caused by the composition is very limited. This is because the inner matrix is either soluble or degradable and the coating, which is relatively thin, is biodegradable, preferably within a short time after the inner matrix has been completely dissolved or degraded.

Due to this fact, the compositions are especially adapted for administration of therapeutic agents which have to be administered regularly, such as insulin, growth hormone etc.

By providing a composition wherein the non-coated part is a contiguous area such as a elongated composition, which is not coated on one or two end surfaces, a zero-order release or substantially zero-order release being known as "psudo zero-order" release can be obtained.

According to a further aspect the invention relates to use of a solid pharmaceutical composition according to the invention for parenteral injection in an animal. The compositions may be injected with or without the use of a trocar or syringe, depending on the strength of the inner matrix.

Compared to liquid formulations containing the same amount of therapeutic agent, a much smaller volume has to be injected when using a composition according to the invention. Therefore, the pain associated with the injection is considerably less.

Furthermore, due to the longer duration of the release of therapeutic agent, the interval between injections can be increased. Furthermore, the invention relates to a method for manufacturing the composition according to the invention. The method may comprise injection moulding, extrusion, or compression followed by coating either through immersion, vapour deposition, or co-extrusion of coat and inner matrix.

DEFINITIONS

"Biodegradable". As used herein a material is biodegradable if it hydrolyses and/or is absorbed into animal tissues such as human tissue when in contact with tissue and/or tissue fluids in an animal.

Inner matrix. As used herein the inner matrix is the core of the composition.

Zero order release: the rate of release of the pharmaceutical agent from the composition is substantially constant over time.

First order release: the rate of release of the pharmaceutical agent from the composition increases/decreases substantially linearly with time.

DETAILED DESCRIPTION

The Biodegradable Water-Impermeable Coating

The role of the biodegradable water-impermeable coating is to reduce the rate of release of the therapeutic agent from the solid composition. The coating will have this effect even if it is partly broken down before the therapeutic agent has been released. Preferably, the coating is water-impermeable at least for a substantial time after the composition has been injected.

According to an especially preferred embodiment of the invention the coating remains water-impermeable until essentially the whole inner matrix has been dissolved. This ensures that the coating exerts the same or substantially the same effect during the whole period of dissolution and/or disintegration of the inner matrix.

Expressed in another way the coating may remain water-impermeable until most of the therapeutic agent has been dissolved. This likewise ensures that the coating exerts the same or substantially the same effect during the whole period of release of therapeutic agent.

The materials that can be used for manufacturing the coat are any materials that fulfil the requirements of biodegradability and water-impermeability, the latter for at least a period.

Suitable examples of coating materials comprise materials selected from the group consisting of polyesters such as polyglycolides, polylactides and polylactic polyglycolic acid copolymers (PLGA); polyglycolide; polylactide; polyethers such as polycaprolactone (PCL); Glycolide, Poly(dl-lactic acid)—MW 20,000-30,000; Poly(dl-lactic acid)—MW 330,000-600,000; Poly(dl-lactic acid)—MW 6,000-16,000; Poly(dl-lactide/glycolide) [50:50]; Poly(dl-lactide/glycolide) [70:30]; Poly(dl-lactide/glycolide) [75:25]; Poly(dl-lactide/glycolide) [80:20]; Poly(dl-lactide/glycolide) [85:15]; Poly(dl-lactide/glycolide) [90:10]; Poly(glycolic acid) [i.v. 1.0-2.0]; Poly(l-lactic acid) [MW 1,600-2,400]; Poly(l-lactic acid) [MW 325,000-460,000]; Poly(l-lactic acid) [MW 40,000-70,000]; Poly(l-lactic acid) [MW 80,000-100,000]; Poly(l-lactide/glycolide) [70:30]; Poly(l-lactide/glycolide) [70:30]; Poly[(−)3-hydroxybutyric acid]; Polycaprolactam (MW 16,000); Polycaprolactam (MW 35,000); Polycaprolactone; Polycaprolactone diol; Polycaprolactone diol (MW 1,250); polyanhydrides; poly(8-hydroxybutyric acid); polyalkyl cyanoacrylates such as no-butyl cyanoacrylate and isopropyl cyanoacetylate; polyacrylamides; poly(orthoesters); polyphosphazenes; polypeptides; polyurethanes; proteins such as albumin, gelatin; carbohydrates such as starch, alginate, chitosan, cellulose; hydrophobic polyamino acids such as polylysin and polyalanin; and mixtures of such polymers.

Preferred materials used for the coat comprise materials selected from the group consisting of polylactic polyglycolic acid copolymer, polyglycolides, and polylactides such as Poly(dl-lactic acid)—MW 20,000-30,000; Poly(dl-lactic acid)—MW 330,000-600,000; Poly(dl-lactic acid)—MW 6,000-16,000; Poly(dl-lactide/glycolide) [50:50]; Poly(dl-lactide/glycolide) [70:30]; Poly(dl-lactide/glycolide) [75:25]; Poly(dl-lactide/glycolide) [80:20]; Poly(dl-lactide/glycolide) [85:15]; Poly(dl-lactide/glycolide) [90:10]; Poly(glycolic acid) [i.v. 1.0-2.0]; Poly(l-lactic acid) [MW 1,600-2,400]; Poly(l-lactic acid) [MW 325,000-460,000]; Poly(l-lactic acid) [MW 40,000-70,000]; Poly(l-lactic acid) [MW 80,000-100,000]; Poly(l-lactide/glycolide) [70:30]; Poly(l-lactide/glycolide) [70:30]; Poly[(−)3-hydroxybutyric acid]; Polycaprolactam (MW 16,000); or Polycaprolactam (MW 35,000).

According to an especially preferred embodiment of the invention, the coating is made essentially from polylactic polyglycolic acid copolymer such as Poly(dl-lactide/glycolide) [50:50]; Poly(dl-lactide/glycolide) [70:30]; or Poly(dl-lactide/glycolide) [75:25]; Poly(dl-lactide/glycolide) [80:20]; Poly(dl-lactide/glycolide) [85:15]; Poly(dl-lactide/glycolide) [90:10]; Poly(l-lactide/glycolide) [70:30]; Poly(l-lactide/glycolide) [70:30]. The advantage of using these polymers for the coating is that their biocompatibility is well documented and that they are listed in the major pharmacopoeias of the world. Polymers of lactic and/or glycolic acid and copolymers of these are hydrolysed within the tissue to their monomer constituents, which are subsequently metabolised by the organism.

By adjusting the degree of cross linking in the coating and by selecting the components of polymers making up the coating it is possible to adjust the degree of biodegradability and the degree of water-impermeability of the coating. Such adjustments are well known in the art. Generally, the higher the molecular weight of the polymers, the slower the rate of degradation of the coat.

Preferably, the thickness of the coating is such that it remains water impermeable until essentially all therapeutic agent has been absorbed. Suitable examples of average thickness are at least 0.5 µm, such as at least 0.75 µm, for example at least 1 µm, such as at least 1.5 µm, for example at least 2 µm, such as at least 2.5 µm, for example at least 5 µm, such as at least 10 µm, for example at least 15 µm, such as at least 20 µm, for example at least 25 µm, such as at least 30 µm, for example at least 40 µm, such as at least 50 µm, for example at least 60 µm, such as at least 70 µm, for example at least 75 µm, such as at least 80 µm, for example at least 90 µm, such as at least 100 µm, for example at least 125 µm, such as at least 150 µm, for example at least 200 µm. The thickness of the coating depends to a large extent on the method used for coating the composition. Thus by co-extrusion of the inner matrix and the coat, a coating thickness from 50 to 200 µm can be obtained. By dipping or spray-coating or vapour deposition a coating thickness of approximately 1 µm can be obtained.

According to an especially preferred embodiment the coating is completely broken down in an animal tissue or tissue fluid more slowly than the time it takes to liberate the therapeutic agent. This is to ensure that the effect of the coating is maintained for longer time than it takes to liberate the therapeutic agent.

It is to be understood that the coating may be broken down within ten times the time it takes to liberate the therapeutic agent, more preferably within five times the liberation time, more preferably within 4 times the liberation time, more preferably within 3 times the liberation time, more preferably within 2.5 times the liberation time, more preferably within 2 times the liberation time, such as within 1.5 times the liberation time. Preferably the coating is broken down as soon as possible after the therapeutic agent has been released from the coat.

It is to be understood that the coating may cover any percentage of the surface of the composition and the covering of any part—however small—will reduce the rate of liberation of therapeutic agent from the composition. Accordingly, the coating may cover at least 5% of the surface of the composition, such as at least 10%, for example at least 15%, such as at least 20%, for example at least 25%, such as at least 30%, for example at least 35%, such as at least 40%, for example at least 45%, such as at least 50%, for example at least 55%, such as at least 60%. More preferably, the coating covers at least 67%, such as at least 70%, more preferably at least 75%, more preferably at least 80%, more preferably at least 85%, more preferably at least 90%, for example at least 91%, such as at least 92%, for example at least 93%, such as at least 94%, such as at least 95%, for example at least 96%, such as at least 97%, for example at least 98%, such as at least 99%, for example at least 99.5%. When more than two thirds of the surface of the composition is coated the effect of the coating is increased.

Preferably the non-coated part of the surface is one, two or a few contiguous area(s). This may be part of the surface located on an end surface of the composition or both end surfaces may be non-coated. Production of the composition is facilitated when the non-coated areas are the end surfaces of the composition. The composition may then be extruded or moulded, be coated and subsequently cut into pieces of the desired length.

Permeable Coat

In order to further reduce the rate of liberation of therapeutic agent, the non-coated part of the surface of the composition is coated by a coat functioning as a membrane. The permeable coat must be permeable to both water and the therapeutic agent as well as to the constituents of the inner matrix. Preferably the permeable coat is made such that diffusion across said permeable membrane is the rate limiting step in liberation of the therapeutic agent. By doing this, the rate of liberation of therapeutic agent can also be efficiently lowered in the case of inner matrices, which dissolve rapidly.

Inner Matrix

The inner matrix may be soluble in water. Examples of this are matrices based on a carbohydrate binder or matrices consisting essentially of the therapeutic agent in the form of a water soluble protein.

The inner matrix may also be degradable in water. The example of this is an inner matrix based on a polymer, which can be broken down by enzymes in the tissue.

Crystalline Inner Matrix

The inner matrix may comprise crystalline material, such as crystalline carbohydrates and/or crystalline therapeutic agent. Such material may advantageously be adapted for extrusion. According to this embodiment, the inner matrix may contain at least 50% (v/v) therapeutic agent, such as at least 60%, for example at least 70%, such as at least 75%, for example at least 80%, such as at least 85%, for example at least 90%, such as at least 95%, for example at least 97%, such as at least 99%, for example essentially 100%. The remaining parts of the inner matrix may comprise binders and/or additives. Any suitable binder may be used, provided that it is acceptable for parenteral use, such as binders mentioned in the European Pharmacopoeia, the Japanese Pharmacopoeia and/or the US Pharmacopoeia. Examples of binders include but are not limited to: carboxymethylcellulose (CMC), fructose, glucose, sucrose, sorbitol, maltose, maltitol, xylito, hydroxypropyl-cellulose, lactose, D-mannitol, MCC, HPC (hydroxypropylcellulose), Na-phosphates, K-phosphates, Ca-phosphates, Na-carbonates and/or Ca-carbonates.

Apart from the binder and the therapeutic agent, the composition may comprise additives, which could be selected from but is not restricted to the group of preservatives, stabilisers, adjuvants, lubricants, and disintegraters. Some therapeutic agents may need to be preserved or stabilised through the use of a preservative or stabiliser, although this is likely to be necessary only in a few cases, owing to the almost anhydrous conditions in the drug formulation. In the cases where the therapeutic agent is for immunisation, it may be preferential to add an adjuvant to increase the immunogenic response.

Also the composition may comprise stabilisers, such as alanine, histidine and glycine.

Compositions comprising crystalline inner matrix and an optional binder may be manufactured according to methods described in e.g. WO 01/26602 (Novo Nordisk A/S).

Glassy Inner Matrix

According to another embodiment the inner matrix may comprise amorphous material, such as for instance a glass, such as described in WO 00/62759 (Novo Nordisk). In such a glassy inner matrix, the therapeutic agent may be dispersed as crystalline particles.

Compositions made according to this embodiment of the invention are particularly adapted for solid-dose parenteral injection through the cutis and/or mucosa, because they have sufficient mechanical strength to be injected without the used of a syringe or trocar.

The glassy inner matrix may for instance comprise a binder and at least one therapeutic agent, said binder constituting at least 0.5% by weight of the composition and said binder comprising at least one binding agent being a carbohydrate, and optionally at least one non-crystallisation agent, whereby said binder forms an amorphous matrix. The binder may constitute from 5-60% by weight of the inner matrix, the remaining part of the inner matrix being essentially therapeutic agent.

According to an especially preferred embodiment, the binder essentially remains an amorphous matrix for at least 6 months at ambient temperature. This is achieved by carefully selecting the binding agent and the optional non-crystallisation agent so that the binding agent does not crystallise during storage. If the binding agent starts crystallising the composition will lose its mechanical strength, or if the crystallisation only takes place at the surface, the geometry of the composition will change and the friction upon injection may increase undesirably.

Furthermore, at least 95% of the strength of the composition may be maintained after 6 months, preferably after 12 months, at ambient temperature. It is important that these compositions are long term stable not only with respect to the biological activity and the structure of the composition, but also that the strength is essentially unaffected by storage. Some binding agents have a propensity to slowly crystallise after the amorphous glass matrix has been formed. Such binding agents are unsuitable for the present embodiment.

The at least one binding agent which together with the optional at least one non-crystallisation agent comprises the binder, may comprise from 50 to 97% by weight of the binder. The preferred amount of binding agent is determined by numerous factors, primarily the actual compound chosen. Some binding agents may form the amorphous glassy matrix of the binder in a pure state and others will need to be mixed with the non-crystallisation agent in various amounts.

When present, the at least one non-crystallisation agent may comprise at least 1% by weight of the binder. In some cases very limited amount such as down to 1% of non-crystallisation agent needs to be present to prevent crystallisation of the binding agent. The amount of non-crystallisation agent is determined largely by the propensity of the binding agent to crystallise.

Many compounds are capable of forming a glass upon melting and subsequent quenching to below the glass transition temperature of the compound, herein designated Tg. Glasses can also be formed by dissolution and subsequent removal of the solvent, whereby the Tg is raised to above the storage and usage temperature. However, most compounds have a propensity to crystallise by themselves. Whereas an amorphous glass matrix often has a high compressive strength and a smooth surface, the same compound in a crystalline state has very limited compressive strength and a rough surface. The present inventors have determined that compositions can be made from pure maltose or from pure sorbitol. These compounds will form glasses, but the compounds crystallise gradually at room temperature causing the strength to be reduced and the geometry to be changed. By mixing two or more compounds, crystallisation can be prevented or retarded. The exact proportion of the two compounds necessary to prevent crystallisation must be determined in each specific case.

The compositions are not necessarily completely water free. However, the water content of the binder is less than 20% (w/w), preferably less than 10%, more preferably less than 5%, such as from 0.1 to 5%, preferably from 1 to 5%. It has been determined that by having a water content between 0.1 and 5%, the composition is not sticky. By lowering the water content even further, the rate of dissolution upon contact with the body fluids may be reduced causing the therapeutic agent to be released very slowly. Furthermore, many therapeutic agents such as proteins, peptides and polypeptides are more stable at a low water content than when completely dry. The advantage of having a low water content is that the therapeutic agent becomes biologically very stable and does not require special storage conditions such as refrigeration to maintain the biological activity. A third advantage is that the composition becomes essentially resistant to microbial attack, since microbes require a certain water content in order to establish a colony. Thus the requirement for handling the compositions become less rigid since the presence of a few microbes on the composition will not result in microbic proliferation and thereby not cause contamination. Finally the presence of excess water in the composition may result in water vapour during processing, which may give rise to air entrapment in the composition during subsequent cooling.

Several compounds may be used as the at least one binding agent and the invention is not limited to any specific compounds. According to a preferred embodiment the at least one binding agent is a mono-, di-, or oligosaccharide or a corresponding sugar alcohol or a derivative thereof. Many of these compounds are frequently used for drug formulation, are contained in the pharmacopoeia and can therefore readily be approved by the authorities. Furthermore, these compounds make an amorphous glassy matrix readily.

Furthermore, the at least one binding agent may be a carbohydrate-derivative. As mentioned, carbohydrates make amorphous glassy matrices readily. In some cases it is preferred to provide the composition with a binder having a slow rate of dissolution compared to binder made from true carbohydrates. This can be obtained by derivatising the carbohydrate, especially by adding non-polar groups to the carbohydrate, whereby the compound is rendered more hydrophobic.

According to a preferred embodiment the at least one binding agent is selected from maltose, sucrose, lactose, cellobiose, trehalose, maltulose, iso-maltulose, maltitol, sorbitol, mannitol, glucose, fructose, raffinose, melezitose, dextran, mannose, sorbose, melibiose, sophrose, turanose, lactulose, stachyose, and xylitol. This group of carbohydrates has excellent amorphous glass matrix making abilities. Furthermore, the carbohydrates are well known and can be purchased at reasonable price and in well characterised grades.

The optional at least one non-crystallisation agent may preferentially also be a carbohydrate, said carbohydrate being different from the binding agent. Likewise, the non-crystallisation agent may be a mono-, di-, or oligosaccharide, a corresponding sugar alcohol, or a derivative. It may be a natural or synthetic carbohydrate and according to an especially preferred embodiment the at least one non-crystallisation agent is selected from maltose, sucrose, lactose, cellobiose, trehalose, maltulose, iso-maltulose, maltitol, sorbitol, mannitol, glucose, fructose, raffinose, melezitose, dextran, mannose, sorbose, melibiose, sophrose, turanose, lactulose, stachyose, and xylitol.

Each combination of binding agent and non-crystallisation agent gives a unique amorphous glass matrix with a unique glass transition temperature, unique solubility, and unique strength. The composition has been found to perform excellently when the binding agent is selected from maltitol, sucrose, sorbitol, and mannitol and the non-crystallisation agent is selected from sorbitol, maltitol, and mannitol. These compounds are often used for pharmaceutical compositions, they all have the advantage of being edible and without any side effects upon administration.

According to an especially preferred embodiment, the binding agent is maltitol and the non-crystallisation agent is sorbitol and/or hydrogenated oligosaccharides. By using these specific compounds to make up the binder, especially excellent results are obtained since the obtained amorphous glass matrix has an optimal glass transition temperature and since the propensity to crystallise is very low. Furthermore, maltitol can be obtained in quantities and in a very suitable grade. Commercial maltitol is made by enzymatically degrading starch whereby a mixture of glucose, maltose, maltotriose and higher saccharides are formed. These are hydrogenated to form their corresponding sugar alcohols sorbitol, maltitol and hydrogenated oligosaccharides. Thus, the product contains primarily maltitol and sufficient amounts of the other sugar alcohols to prevent the crystallisation. Maltitol is tissue compatible, it is a well tested compound and has been used for years in the production of so-called sugarfree candies.

The binder comprising the at least carbohydrate and the optional at least one non-crystallisation agent should not reduce the stability of the therapeutic agent. This could for instance take place via chemical reactions between the therapeutic agent and the components of the binder, either during processing or during storage. To avoid undesired reactions between aldehyde groups in reducing sugars and side chains of proteins, peptides, or polypeptides, the at least one carbohydrate and the at least one non-crystallisation agent are preferentially chosen from the group of non-reducing sugars.

The Tg of the binder in the final composition should preferably be at least 30° C. The Tg of the binder should be above ambient temperature, preferably 5 to 10° C. above ambient temperature, or the composition will gradually melt during storage. Under certain special conditions, it may be necessary to select a binder having a higher Tg, e.g. for use in the tropics. With certain very heat labile therapeutic agents, it may be necessary to select a binder having a much lower Tg, so that the composition can be processed at e.g. 50° C. With such a low Tg, it may be necessary to store the compositions cold at 50° C. and to inject them before the temperature rises above the Tg.

The invention is not limited by an upper Tg of the binder. Binders having a Tg from 40 to 120° C. are preferred. Depending on the therapeutic agent, it is preferred that the Tg of the binder is less than 90° C., more preferably less than 80° C. A majority of therapeutic agent are heat labile and although many proteins or peptides can tolerate exposure to elevated temperatures in a dry state a loss of activity may nevertheless be encountered during processing. To reduce exposure of the therapeutic agent to elevated temperatures it is therefore preferable to select binders with a low Tg with due respect to the lower limits mentioned above.

According to a preferred embodiment, the viscosity of the composition is less than 50,000 Pa*s, preferably less than 40,000 Pa*s, more preferably from 1,000 to 30,000 Pa*s, in a sub-range of the temperature interval between 60 and 140° C. In this temperature interval the composition is in the state of a melt, which can be shaped. Generally, most glasses encompassed by the present embodiment have a suitable viscosity for bringing into the desired geometry at 20 to 30° C. or even approximately 40° C. above Tg of the binder. The viscosity of the composition is very important during injection of the melt into the mould and furthermore in the embodiments where the therapeutic agent is mixed with the melted binder.

The composition may also be injection mouldable in a sub-range of the same temperature interval. A preferred method for manufacturing the composition is by injection moulding. This means that the composition should possess a certain viscosity e.g. 1,000 to 30,000 Pa*s in at least a sub-range of the temperature interval 60 to 140° C.

Release of the Therapeutic Agent

By carefully selecting the coating, the area of coating and the thickness of the coating, the composition may be designed to have almost any release profile, which is longer and/or more constant than the release profile of a non-coated composition. According to an especially preferred embodiment, at most 70% of the therapeutic agent is released from the composition within 50% of the total release time after administration. This compares with the non-coated counterpart in which the release is much more rapid, so that 80-90% of the therapeutic agent is released within 50% of the total release time after administration.

More preferably at most 60% of the therapeutic agent is released from the composition within 50% of the total release time after administration.

The total release period depends on the specific composition. The majority of the embodiments falling under the scope of the invention are compositions comprising therapeutic agents, which are to be released within hours or days or up to a week. Accordingly, at least 95% of the therapeutic agent may be released within one week, such as within 6 days, for example within 5 days, such as within 4 days, for example within 48 hours, such as within 47 hours, for example within 46 hours, such as 45 hours, for example 44 hours, such as 43 hours, for example 42 hours, such as 41 hours, for example 40 hours, such as 39 hours, for example 38 hours, such as 37 hours, for example 36 hours, such as 35 hours, for example 34 hours, such as 33 hours, for example 32 hours, such as 31 hours, for example 30 hours, such as 29 hours, for example 29 hours, such as 28 hours, for example 27 hours, such as 26 hours, for example 26 hours, such as 25 hours, for example 24 hours, such as 23 hours, for example 22 hours, such as 21 hours, for example 20 hours, such as 19 hours, for example 18 hours, such as 17 hours, for example 16 hours, such as 15 hours, for example 14 hours, such as 13 hours, for example 12 hours such as 11 hours, for example 10 hours, such as 9 hours, for example 8 hours, such as 7 hours, for example 6 hours, such as 5 hours, for example 4 hours, such as 3 hours, for example 2 hours, such as 1 hour.

According to an especially preferred embodiment of the invention, the therapeutic agent is released as a pseudo 0-order release. This can for instance be obtained through a composition, from which release takes place through an opening (non-coated part of the surface) having a constant area. As illustrated by the attached examples this is one example of a composition having approximate zero-order release.

According to another embodiment, the therapeutic agent may be released as a first order release. This could be obtained by giving the composition the shape of a cone, which is non-coated on the planar surface. Thus during release, the area from which therapeutic agent is released decreases at an approximately constant rate, and the rate of release of the therapeutic agent decreases at an approximately constant rate.

Therapeutic Agents

The composition may comprise any therapeutic agent, such as an agent is selected from analgesics, antianxiety drugs, antiarthiritic drugs, antibiotic agents, anticholinergics, antidepressants, antidiabetics, antiemetics, antihistaminics, antihypertensive agents, antiinflammatory drugs, antimigraine agents, antiparkinsonism agents, antipasmodesics, antipsychotics, antithrombotic agents, antiviral agents, appetite suppressants, blood factors, cardiovascular drugs, cerebral vasodilators, chemotherapeutic drugs, cholinergic agonists, contraceptives, coronary agents, diuretics, hormonal agents, immunosuppressive agents, growth factors, narcotic antagonists, opioids, peripheral vasodilators, tranquilizers, vaccines, immunogenic agents, and immunising agents.

Likewise the therapeutic agent may be selected from hormones, lipids, nucleic acids, nucleotides, oligonucleotides, oligosaccharides, organics, peptide mimetics, antibodies, peptides, polysaccharides, and proteins.

Preferably, the therapeutic agent is selected from proteins, peptides, and polypeptides, said protein, peptide, or polypeptide being amorphous or crystalline.

The composition according to the invention is particularly suitable for administering therapeutic agents selected from hormones, antidiabetic drugs, growth factors, and blood factors, preferably being a protein selected from insulin, glucagon, growth hormone, coagulation factors such as FVII and FVIII, GLP-1, EPO, TPO, interferon or derivatives of these proteins. Due to the possibility for approximate zero order release the composition is especially adapted for administration of therapeutic agents, which have to be present in a certain amount in the tissue and/or tissue fluids.

Most preferably, the therapeutic agent is insulin or a derivative thereof such as: an insulin hexamer, crystals of insulin, insulin cross-linked to protamin (for example marketed as Protafan® by Novo Nordisk), insulin cross-linked to zinc, acidic crystals of insulin, insulin precipitated with block-copolymers.

The amount of therapeutic agent in the composition should be as high as possible in order to keep the total volume of the composition low. It is thus anticipated that the therapeutic agent comprises at least 25% by weight of the composition, preferably more than 30%, more preferably more than 40%, such as more than 50%, for example more than 60%, such as more than 70%, for example more than 75%, such as more than 80%, for example more than 90%, such as more than 95%.

The composition is especially adapted for regular administration so that one composition contains one dose of the therapeutic agent. The composition may also contain fractions of a dose, such that one dose corresponds to 2, 3, 4, 5, 6 or up to 10 compositions that can be administered at the same time.

Other Components of the Inner Matrix

In the cases where the composition comprises other components apart from the therapeutic agent the optional other components of the inner matrix should not reduce the stability of the therapeutic agent.

The solubility of of the optional other components of the inner matrix can be either higher or lower than the solubility of the therapeutic agent.

Examples of other components include but are not limited to preservatives, adjuvants, stabilisers.

Physical Features of the Composition

Preferentially, the composition should be essentially free from entrapped air. It is very important for the strength of the composition that no air is trapped inside the composition during processing in order to prevent air in the composition after cooling. Apart from reducing the strength, entrapped air also takes up unnecessary space and thereby reduces the amount of therapeutic agent contained in the composition.

The composition preferentially has the shape of a pellet wherein the cross section of the pellet is substantially circular, triangular, square, or polygonal. According to an especially preferred embodiment, the composition has the shape of a rod essentially cylindrical and pointed at one end.

It is also contemplated that the compositions according to the present invention are in the shape of microbeads, which are coated on part of their surface. Compared to non-coated microbeads these give a more constant rate of release because the initial peak observed with non-coated microbeads is reduced.

The top radius of the tip is preferably below half of the diameter of the composition as such, more preferably below a fourth of the diameter of the composition as such.

By this embodiment is obtained that the composition acts like a needle and can penetrate the cutis or mucosa of the patient in the same way as a hypodermic needle to enter the subcutis or submucosa. Thereby less force is required to force the composition through the cutis or mucosa.

When the composition has the shape of a needle it is especially important the composition remains stable and the tip does not deteriorate.

As a human skin model, porcine abdomen skin has been used in penetration tests. Graphite rods with differently shaped pointed ends are pressed into porcine skin with a Lloyd Instrument LR5K, UK. The pressure force is measured in Newton as a function of the distance. The maximum force is used to compare different rod shapes. If the rods have no point (top angle=180°) the rod breaks before entering the skin. Using a graphite rod with a cone shaped point (90° top angle) is sufficient to penetrate the skin. However, a top angle of 60° significantly improves the penetration of the skin. The rod is preferably as pointed as possible, however, points with an angle below 10° are very thin and thereby fragile. In conclusion, the top angle of the pointed end should preferably be between 10 and 110°, preferably between 20 and 90°, more preferably between 30 and 70°, if the composition is going to be injected without the use of a trocar or syringe.

Strength

By the term strength is meant that the composition has sufficient compressive strength to penetrate the skin of a patient. It has been determined experimentally that a pressure force of less than 5 Newton is required to penetrate the epidermis of a human being with the claimed composition. Less is required to penetrate the mucosa. Consequently, compositions for parenteral injection must be able to withstand such pressure force.

The strength can be tested in a force gauge tester such as an Advanced Force Gauge AFG-250N from Mecmesin, UK. Tests are carried out by formulating the composition as a rod and applying a pressure force to the rod. The pressure force is increased until the rod breaks. The instrument records the pressure force necessary to break the rod. This parameter is termed the compressive strength and should be understood as the breaking strength under compression.

According to a preferred embodiment, a rod-shaped composition is able to withstand a pressure force of at least 10 Newton. According to another embodiment, a rod made from the composition is able to withstand a pressure force of at least 5 Newton. Thereby, the composition has a well-defined compressive strength, which is furthermore sufficient to endure the force required to penetrate the epidermis.

According to other embodiments, the compositions are injected with the use of a trocar. Such compositions do not need such a strength.

Shape

The composition is preferably in the form of a pellet. The cross section of the pellet may be substantially cylindrical, triangular, square or polygonal.

Preferably the composition has the shape of a rod being essentially cylindrical. The composition may have a constant cross section in the longitudinal direction which facilitates production and in combination with one or two non-coated ends ensures an approximate zero-order release. However, the composition may also have a variable cross section in the longitudinal direction. This could potentially give a variable release rate according to the variation in the cross section.

Further examples of shapes of the composition include the shape of a bead, a sphere, a hemisphere, a cube, a cone, a prism, and an irregular shape.

Size

The composition may have a maximum cross section of less than 2 mm, such as less than 1 mm, preferably from 0.7 to 0.3 mm, more preferably 0.6 to 0.4 mm. By providing the composition with this thickness, it has been determined that it can be injected with very little or essentially without pain. A further advantage is that less force is required to penetrate the skin as the diameter is reduced. By rods formed of the composition according to the invention, it has been found that even at these dimensions they still have the necessary strength to penetrate the cutis or mucosa upon injection. However, a too small diameter will require a very long composition in order to contain the predetermined amount of therapeutic agent. A too small diameter would also reduce the compressive strength of the composition and maybe cause it to break upon injection.

The composition may be manufactured in any length but for most applications, the length of the rod is less than 10 mm, preferably less than 8 mm, more preferably less than 6 mm. The length of the composition is determined by the dose of the therapeutic agent, the amount of binder required if any, and the selected diameter. The dose of many therapeutic proteins is approximately 1 mg. One mg of protein excluding binder corresponds approximately to a cylinder with a diameter of 0.5 mm and a length of 3 mm. If such a composition containing 1 mg of protein is made from 50% therapeutic agent and 50% binder, the composition has a length of 6 mm. When the required dose is smaller, the dimension of the composition will be reduced accordingly. A dose of ⅓ mg protein in a composition with 50% binder for the inner matrix and having a diameter of 0.5 mm has an approximate length of 2 mm. The invention is not restricted to any specific volume, the volume being determined by the length and diameter of the composition. In most cases, the volume of the composition is less than 5 µl, such as less than 4 µL, for example less than 3 µL, such as less than 2 µL, for example less than 1 µl. Volumes down to 0.25 µl can be obtained for small doses of therapeutic agent. Thus, the above-mentioned composition having a diameter of 0.5 mm and a length of 2 mm has a volume of 0.39 µl.

The composition may have sufficient strength to be able to penetrate the epidermis or mucosa of a human being with a force less than 5 Newton without the use of a trocar or syringe. This greatly facilitates administration and decreases the risk of cross contamination between and among patients and has the advantage that trocars and/or syringes are not necessary In other embodiments the composition is adapted to be injected using a trocar or a syringe, in which case strength is not an important parameter.

Methods for Manufacturing the Composition

The compositions according to the present invention may be manufactured in a number of different ways, primarily depending on the structure of the inner matrix.

Basically the method may comprise shaping the inner matrix comprising at least one therapeutic agent into a pellet, and subsequently coating said pellet with a biodegradable polymer. The coated pellet may advantageously be cut into elongated compositions. These compositions will then only be coated on the longitudinal surfaces and be non-coated on the cut end surfaces. Preferably the pellet is in the shape of a rod.

The compositions may be shaped either by extrusion, injection moulding, and/or compression. Injection moulding is especially suitable for compositions wherein the inner matrix comprises a glassy carbohydrate-based binder.

Coating may be performed either by dipping the pellet into a solution of the biodegradable polymer, by spraying the pellet with a formulation of the biodegradable polymer, or by vapour deposition of a formulation of the biodegradable polymer on the pellet, followed by drying. These methods will give relatively thin coatings in the vicinity of 1 µm or thicker depending on the viscosity of the solution of biodegradable polymer and/or the time used for spraying or vapour deposition.

Coating may also comprise co-extrusion of the inner matrix and the coat, which will generally result in a thicker coat in the size of 100 µm.

It is essential that only part of the surface of the finished compositions are coated with biodegradable polymer. This may be obtained by coating only part of the surface of the composition with biodegradable polymer, or by making at least one hole in the biodegradable polymer after coating. The at least one hole may be made by cutting a rod as described above, but it can also be performed by using of a laser for making the at least one hole. When making the hole in the coating, it is important that the variation in the size (area) of the non-coated part is kept to a minimum, preferably the standard error of the mean of the area is less than 5%.

Another way of providing the composition with a coating is through coating a mould with a biodegradable polymer, melting and injecting an inner matrix comprising at least one therapeutic agent into the mould, and after hardening, cutting the resulting rod into elongated compositions being non-coated on the end surfaces.

EXAMPLES

Example 1

Release Profiles

A simple computer simulation on a model for diffusion from different geometries shows the principle of delaying the absorption by coating parts of the surface.

The model consists of three distinct zones:
1. Solid material
2. Diffusion layer
3. Zone with free flow The geometry of the model is arranged so that Zone 1 is completely surrounded by Zone 2 which in turn is completely surrounded by Zone 3. Zone 1 is the drug and the binder on a solid form, for example as a glass. On the surface of Zone 1, the material enters Zone 2 (that is, the material is dissolved) in which it is allowed to diffuse according to Fick's first law of diffusion. Material that enters Zone 3, in which there is free flow, is removed fast and is considered to have been absorbed.

In the following, a few different situations are considered:

Firstly, a situation in which the solid material is deposited symmetrically around a centre.

Figure 1:
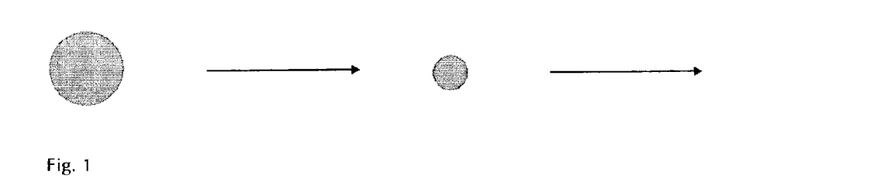
FIG. 1 shows the development of the composition in time when no coating is present.

FIG. 1 shows the development of the composition in time when no coating is present.

Figure 2:
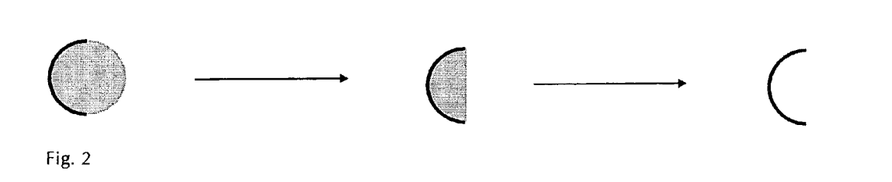
FIG. 2 shows the development of the composition in time when half the surface is coated.

FIG. 2 shows the development of the composition in time when half the surface is coated.

Figure 3:
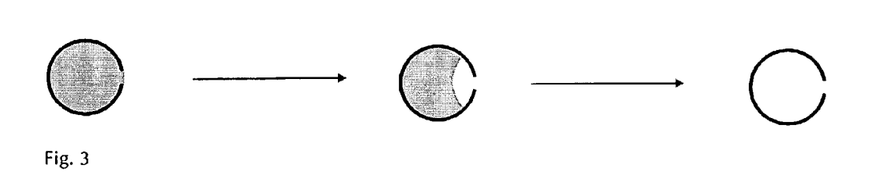
FIG. 3 shows the development of the composition in time when only a small part of the composition is left open.

FIG. 3 shows the development of the composition in time when only a small part of the composition is left open.

Figure 4:
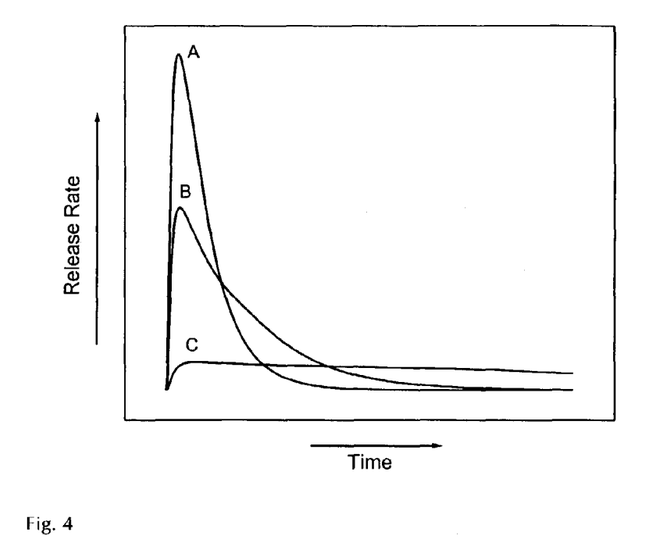
FIG. 4 shows a graph of the release of material from the composition as a function of time for each of the cases shown in FIGS. 1, 2 and 3. A corresponds to the composition of FIG. 1. B corresponds to the composition of FIG. 2. C corresponds to the composition of FIG. 3.

FIG. 4 shows a graph of the release of material from the composition a function of time for each of the cases A, B and C. Curve A (composition of FIG. 1): It is evident that the uncoated composition is characterised with a rapid increased in the release of material followed by a slower slow decay. (This profile is not unlike the release profile obtained when human insulin is injected into a patient.). Curve B (composition of FIG. 2): When half the surface is coated, the peak value is almost half that of the uncoated and the duration of the release is also prolonged. Curve C (composition of FIG. 3): When only a small fraction of the surface is uncoated there is almost no peak and the release is almost constant for a long period corresponding to a 0 order release.

Figure 5:
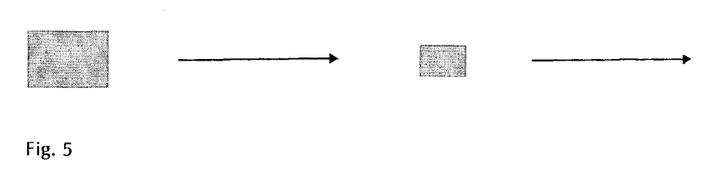
FIG. 5 shows the erosion of the elongated composition in time when the composition is uncoated.

Secondly, a situation in which the material is deposited as an elongated form:

FIG. 5 shows the development of the elongated composition in time when the composition is uncoated.

Figure 6:
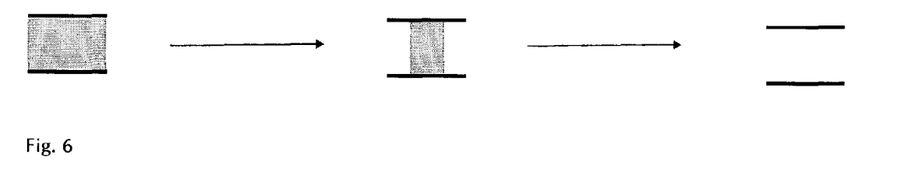
FIG. 6 shows the erosion when only the ends are uncoated.

FIG. 6 shows the development when only the ends are uncoated.

Thirdly, an even more elongated form is considered.

Figure 7:
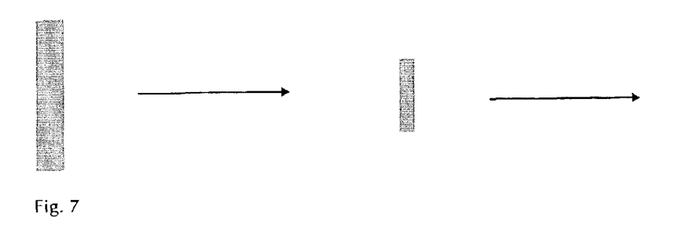
FIG. 7 shows the erosion of the composition in time when the composition is uncoated.

FIG. 7 shows the development of the composition in time when the composition is uncoated.

Figure 8:
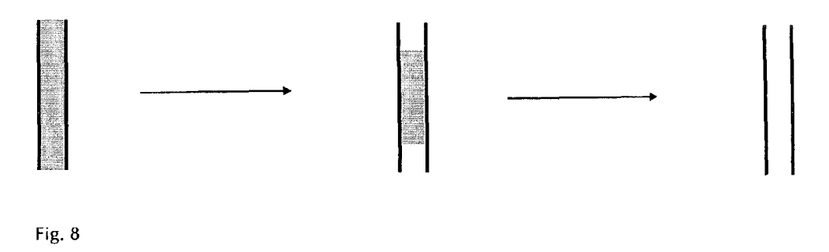
FIG. 8 shows the erosion when only the ends are uncoated.

FIG. 8 shows the development when only the ends are uncoated.

Figure 9:
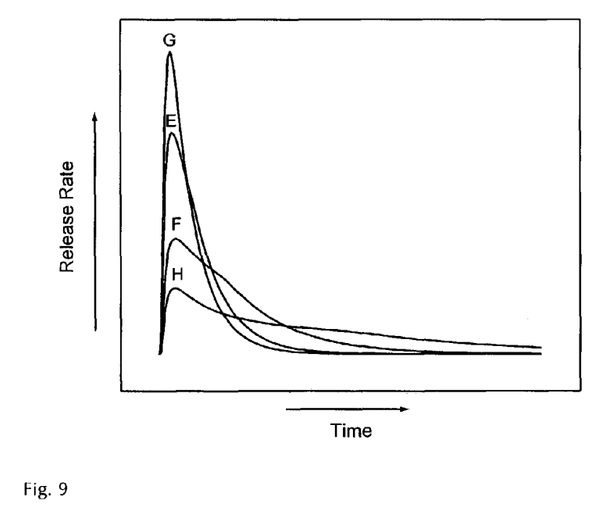
FIG. 9 shows a graph of the release of material from the composition as a function of time. E corresponds to the composition of FIG. 5. F corresponds to the composition of FIG. 6. G corresponds to the composition of FIG. 7. H corresponds to the composition of FIG. 8.

FIG. 9 shows a graph of the release of material from the composition a function of time for each of the cases E (FIG. 5), F (FIG. 6), G (FIG. 7) and H (FIG. 8).

Example 2

Manufacture of a Composition

Extruded Composition Containing 100% Human Insulin 1.0 g of insulin is mixed with 1.0 g of water. The mixture was kneaded with a spatula in a glass bottle until homogeneity. The mixture was placed in a Ray-Ran test sample moulder from Ray-Ran Engineering, UK. The mixture was extruded through a 0.5 mm hole. The resulting rods were dried for 24 hours. The compressive strength was tested with an Advanced Force Gauge AFG-250N from Mecmesin, UK. The compressive strength of the rods (diameter 0.5 mm, length 5 mm) was between 2 and 5 N and the rods were therefore not able to penetrate human skin, but had to be administered using a trocar or syringe. The rods were investigated under microscope and air entrapment was observed.

Extruded Composition Containing 80% Human Insulin and 20% Mannitol 0.4 g of mannitol was dissolved in 3.6 g water. 1.6 g of insulin is mixed with the mannitol solution. The mixture was kneaded with a spatula in a glass bottle until homogeneity. The mixture was placed in a Ray-Ran test sample moulder from Ray-Ran Engineering, UK. The mixture was extruded through a 0.5 mm hole. The resulting rods were dried for 24 hours. The compressive strength was tested with an Advanced Force Gauge AFG-250N from Mecmesin, UK. The compressive strength of the rods (diameter 0.5 mm, length 5 mm) was between 1 and 5 N and the rods were therefore not able to penetrate human skin, but could be administered using a trocar or syringe. The rods were investigated under microscope and air entrapment was observed.

These examples illustrate one way of manufacturing the inner matrix through extrusion with or without a binder. These composition do not have the physical strength to be parenterally injected. One of the reasons for the lack of strength is the presence of entrapped air. Thus, such compositions will need to be injected by use of a hypodermic needle, a trocar or similar means.

Composition Comprising a Binder, 100% C*Maltidex H16323 (88% Maltitol)

100 g C*Maltidex H16323 was cooked at 168° C. with 8 minutes vacuum time in the end. The solution was cooled to 100° C. and transferred to the Ray-Ran test sample moulder from Ray-Ran Engineering, UK and extruded through a 0.5 mm hole. The amorphous glassy rod was cooled to room temperature. The compressive strength was tested with an Advanced Force Gauge AFG-250N from Mecmesin, UK. The compressive strength of the rods (diameter 0.5 mm, length 5 mm) was between 30 and 50 N and therefore suited to penetrate human skin. The compressive strength of the dry C*Maltidex rods are comparable with HB type pencil from Pentel, Japan.

This example illustrates that it is possible to manufacture the inner matrix of the compositions with a very high strength. In the specific example a composition was moulded from C*Maltidex which contains 88% maltitol. This product contains in itself sufficient "impurities", primarily sorbitol and sugar alcohols of maltotriose and higher oligosaccharides, acting as non-crystallisation agents.

Composition Comprising 50% Binder 50% Insulin.

35 g of dry amorphous C*Maltidex H16323 was mixed with 35 g human insulin in a Brabender with a Plasti-Corder PL2000 and Mixer Measuring Head at 95° C. until the torque in Nm was constant. The mixture was cooled and investigated under microscope and there was no air entrapment, which also is indicated by the constant torque. The activity of insulin was measured before and after the mixing at 95° C. using the pharmacopoeia HPLC method. The cooled mixture has no air entrapment. The insulin activity before mixing was 99.62% and after mixing 97.52%. The difference is not significant.

The example illustrates the advantage of preparing a composition without adding water. Although the melt is prepared at 95° C., the reduction in insulin activity is negligible. This is primarily a consequence of the almost anhydrous state of the glass matrix. Many heat labile therapeutic agents, typically proteins, polypeptides and peptides, tolerate relatively high temperatures in the absence of water.

Example 3

Dip-Coating with PLGA.

A 10% solution of poly lactic acid-glycolic acid copolymer with a lactic acid/glycolic acid ratio in the polymer of 75/25 was perpared in methylene chloride. The elongated compositions according to example two were immersed into the solution and left to dry at room temperature. The coating layer had a thickness of 0.14 mm. After dipping and drying, the elongated compositions were cut thereby leaving both ends of the compositions un-coated.

The invention claimed is:

1. A solid pharmaceutical composition for parenteral administration comprising:
an inner matrix comprising:
at least one therapeutic agent, and
a binder constituting at least 0.5% by weight of the composition and comprising a binding agent, wherein the binding agent is a carbohydrate and the binder forms an amorphous matrix with the components of the inner matrix;
a biodegradable and water-impermeable coating covering at least 50% of the exterior surface of the inner matrix of said composition, the coating having a coating area and a coating thickness;
at least one non-coated area on the exterior surface of the inner matrix of said composition; and
a permeable coat over the at least one non-coated area,
wherein the rate of release of the therapeutic agent can be controlled by the at least one non-coated area,
wherein the release profile of the therapeutic agent can be controlled by at least one of the coating, the coating area, and the coating thickness to provide a release profile which is longer, more constant or longer and more constant than a release profile of a non-coated composition, and
wherein said inner matrix disintegrates upon contact with animal tissue or tissue fluids and the solid pharmaceutical composition is of sufficient strength such that it is capable of parenteral administration by penetrating the epidermis or the mucosa of a patient by itself and without the assistance of a trocar or syringe.

2. The composition according to claim 1, wherein the coating is made from a material selected from the group consisting of polyglycolides; polylactides; polylactic polyglycolic acid copolymers (PLGA); polyglycolide; polylactide; polycaprolactone (PCL); Glycolide;
Poly(dl-lactic acid)-MW 20,000-30,000;
Poly(dl-lactic acid)-MW 330,000-600,000;
Poly(dl-lactic acid)-MW 6,000-16,000;
Poly(dl-lactide/glycolide) [50:50];
Poly(dl-lactide/glycolide) [70:30]; Poly(dl-lactide/glycolide) [75:25];
Poly(dl-lactide/glycolide) [80:20]; Poly(dl-lactide/glycolide) [85:15];
Poly(dl-lactide/glycolide) [90:10]; Poly(glycolic acid) [i.v. 1.0-2.0];
Poly(l-lactic acid) [MW 1,600-2,400]; Poly(l-lactic acid) [MW 325,000-460,000]; Poly(l-lactic acid) [MW 40,000-70,000];
Poly(l-lactic acid) [MW 80,000-100,000];
Poly(l-lactide/glycolide) [70:30];
Poly[(-)3-hydroxybutyric acid]; Polycaprolactam (MW 16,000);
Polycaprolactam (MW 35,000); Polycaprolactone;
Polycaprolactone diol; Polycaprolactone diol (MW 1,250); polyanhydrides; poly(8-hydroxybutyric acid); nobutyl cyanoacrylate; isopropyl cyanoacetylate; polyacrylamides; poly(orthoesters); polyphosphazenes; polypeptides; polyurethanes; albumin; gelatin; starch; alginate; chitosan; cellulose; polylysin and polyalanin; and a mixture of one or more of the foregoing polymers.

3. The composition according to claim 2, wherein the coating is made from a material selected from the group consisting of polylactic polyglycolic acid copolymer; polyglycolides; Poly(dl-lactic acid)—MW 20,000-30,000;
Poly(dl-lactic acid)—MW 330,000-600,000; Poly(dl-lactic acid)—MW 6,000-16,000; Poly(dl-lactide/glycolide) [50:50]; Poly(dl-lactide/glycolide) [70:30];
Poly(dl-lactide/glycolide) [75:25]; Poly(dl-lactide/glycolide) [80:20];
Poly(dl-lactide/glycolide) [85:15]; Poly(dl-lactide/glycolide)[90:10];
Poly(glycolic acid) [i.v. 1.0-2.0]; Poly(l-lactic acid) [MW 1,600-2,400];
Poly(l-lactic acid) [MW 325,000-460,000]; Poly(l-lactic acid) [MW 40,000-70,000]; Poly(l-lactic acid) [MW 80,000-100,000]; Poly(l-lactide/glycolide) [70:30]; Poly[(−)3-hydroxybutyric acid]; Polycaprolactam (MW 16,000); and Polycaprolactam (MW 35,000).

4. The composition according to claim 2, wherein the coating consists essentially of Poly(dl-lactide/glycolide) [50:50]; Poly(dl-lactide/glycolide) [70:30];
Poly(dl-lactide/glycolide) [75:25]; Poly(dl-lactide/glycolide) [80:20];
Poly(dl-lactide/glycolide) [85:15]; Poly(dl-lactide/glycolide) [90:10]; or Poly(llactide/glycolide) [70:30].

5. The composition according to claim 1, wherein the coating has an average thickness of at least 0.5 µm.

6. The composition according to claim 1, wherein the coating covers at least 55% of the exterior surface of the inner matrix of the composition.

7. The composition according to claim 1, wherein a non-coated part of the surface is one contiguous area.

8. The composition according to claim 1, wherein a non-coated part of the surface is located on an end surface of the composition.

9. The composition according to claim 8, wherein both end surfaces are non-coated.

10. The composition according to claim 1, wherein diffusion across said permeable membrane is the rate limiting step in liberation of the therapeutic agent.

11. The composition according to claim 1, wherein the inner matrix is soluble in water.

12. The composition according to claim 1, wherein the inner matrix is degradable in water.

13. The composition according to claim 1, wherein the inner matrix comprises crystalline material.

14. The composition according to claim 13, wherein the inner matrix comprises extruded material.

15. The composition according to claim 13, wherein the inner matrix contains at least 50% (v/v) therapeutic agent.

16. The composition according to claim 1, wherein the amorphous matrix comprises a glass.

17. The composition according to claim 1, wherein the binder constitutes from 5-60% by weight of the inner matrix.

18. The composition according to claim 17, wherein the water content of the binder is less than 20% by weight.

19. The composition according to claim 1, wherein the at least one binding agent is selected from maltose, sucrose, lactose, cellobiose, trehalose, maltulose, isomaltulose, maltitol, sorbitol, mannitol, glucose, fructose, raffinose, melezitose, dextran, mannose, sorbose, melibiose, sophrose, turanose, lactulose, stachyose, xylitol.

20. The composition according to claim 17, wherein the binding agent is selected from maltitol, sucrose, xylitol, sorbitol, and mannitol and the noncrystallisation agent is selected from sorbitol, xylitol, maltitol, and mannitol.

21. The composition according to claim 17, wherein the Tg (glass transition temperature) of the binder is at least 30° C.

22. The composition according to claim 21, wherein Tg of the binder is from 40 to 120° C.

23. The composition according to claim 1, wherein the viscosity of the inner matrix is less than 50,000 Pa*s, in a sub-range of the temperature interval between 60 and 140° C.

24. The composition according to claim 1, wherein the inner matrix is injection mouldable in a sub-range of the temperature interval between 60 and 140° C.

25. The composition according to claim 1, wherein at most 70% of the therapeutic agent is released from the composition within 50% of the total release time after administration.

26. The composition according to claim 25, wherein at most 60% of the therapeutic agent is released from the composition within 50% of the total release time after administration.

27. The composition according to claim 1, wherein at least 95% of the therapeutic agent is released within one week.

28. The composition according to claim 1, wherein the therapeutic agent is released as a pseudo 0-order release.

29. The composition according to claim 1, wherein the therapeutic agent class is selected from the group consisting of hormones, antidiabetic drugs, growth factors, insulin, glucagon, growth hormone, coagulation factors, FVII and FVIII, GLP-1, EPO, TPO, and interferon.

30. The composition according to claim 1, wherein the therapeutic agent comprises at least 25% by weight of the composition.

31. The composition according to claim 1, comprising one dose of the therapeutic agent.

32. The composition according to claim 1, further comprising an additive selected from the group consisting of preservatives, adjuvants, stabilisers, lubricants, and disintegraters.

33. The composition according to claim 1, wherein the composition can endure a pressure force of at least 10 Newton.

34. The composition according to claim 1, wherein the composition can endure a pressure force of at least 5 Newton.

35. The composition according claim 1, wherein at least 95% of the strength of the composition is maintained after 6 months, at ambient temperature.

36. The composition according to claim 1, being pointed at one end.

37. The composition according to claim 36, wherein the top angle of the rod is between 10 and 110°.

38. The composition according to claim 1, having the shape of a sphere, a hemisphere, a cube, a cone, a prism, or an irregular shape.

39. The composition according to claim 1, wherein the volume of the composition is less than 5 µL.

40. The composition according to claim 1, wherein the composition can penetrate the epidermis or mucosa of a human being with a force less than 5 Newton without the use of a trocar or syringe.

41. The composition according to claim 39, wherein the volume of the composition is less than 4 µL.

42. The composition according to claim 39, wherein the volume of the composition is less than 3 µL.

43. The composition according to claim 39, wherein the volume of the composition is less than 2 µL.

44. The composition according to claim 39, wherein the volume of the composition is less than 1 µL.

45. The composition of claim 1, wherein the binder further comprises at least one non-crystallisation agent.

46. The composition of claim 1, wherein the coating has an average thickness of 0.5 to 200 µm.

47. The composition according to claim 45, wherein the at least one non-crystallisation agent does not reduce the stability of the therapeutic agent.

48. The composition according to claim 45, wherein the solubility of the at least one non-crystallisation agent is higher than the solubility of the therapeutic agent.

49. The composition according to claim 45, wherein the solubility of the at least one non-crystallisation agent is lower than the solubility of the therapeutic agent.

* * * * *

UNITED STATES PATENT AND TRADEMARK OFFICE
CERTIFICATE OF CORRECTION

| | | |
|---|---|---|
| PATENT NO. | : 8,454,997 B2 | Page 1 of 1 |
| APPLICATION NO. | : 10/322143 | |
| DATED | : June 4, 2013 | |
| INVENTOR(S) | : Hansen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 878 days.

Signed and Sealed this
Third Day of March, 2015

Michelle K. Lee
*Deputy Director of the United States Patent and Trademark Office*